US008481740B2

(12) United States Patent
Farkas (Nee Dahan) et al.

(10) Patent No.: US 8,481,740 B2
(45) Date of Patent: Jul. 9, 2013

(54) IMIDAZO[1,2 A] PYRIDINE-6-CARBOXAMIDE DERIVATIVES, THEIR USE FOR THE TREATMENT OF COLON CANCER AND THEIR METHOD OF MANUFACTURE

(75) Inventors: Nurit Esperance Farkas (Nee Dahan), Johannesburg (ZA); Hajierah Davids, Port Elizabeth (ZA); Candice Langley, Johannesburg (ZA); Charles Bernard De Koning, Edenvale (ZA)

(73) Assignee: University of the Witwatersrand, Johannesburg, Johannesburg (ZA)

( * ) Notice: Subject to any disclaimer, the term of this patent is extended or adjusted under 35 U.S.C. 154(b) by 0 days.

(21) Appl. No.: 13/263,172

(22) PCT Filed: Apr. 1, 2010

(86) PCT No.: PCT/IB2010/051427

§ 371 (c)(1),
(2), (4) Date: Dec. 14, 2011

(87) PCT Pub. No.: WO2010/116302

PCT Pub. Date: Oct. 14, 2010

(65) Prior Publication Data

US 2012/0101122 A1 Apr. 26, 2012

(30) Foreign Application Priority Data

Apr. 7, 2009 (ZA) ................................ 2009/00360

(51) Int. Cl.
*C07D 471/04* (2006.01)

(52) U.S. Cl.
USPC ........................................................ 546/121

(58) Field of Classification Search
USPC .................................. 546/113, 121; 514/300
See application file for complete search history.

(56) References Cited

U.S. PATENT DOCUMENTS 6,849,642 B2 * 2/2005 Gerlach et al. ................ 514/300
2010/0173930 A1 * 7/2010 Muci et al. .................... 514/300

FOREIGN PATENT DOCUMENTS

WO 2007/067711 * 6/2007

OTHER PUBLICATIONS

Zips et. al., "New Anticancer Agents: In Vitro and In Vivo Evaluation", In Vivo 19:1-8 (2005).*

* cited by examiner

*Primary Examiner* — Patricia L Morris
(74) *Attorney, Agent, or Firm* — Ladas & Parry LLP

(57) ABSTRACT

This invention relates to the manufacture of novel chemical compounds which have biological activity, particularly to novel chemical compounds that are cytotoxic against colon cancer cells and colon cancer cell lines. The manufacturing of said chemical compounds displaying anti-cancer properties employs the use of multi-component chemical reactions. The object of this invention is to manufacture and isolate analogues of imidazo[1,2-a]pyridine, namely compounds of Formula 1, which are cytotoxic against colon cancer cells, while concomitantly being relatively inactive against white blood cells.

Formula 1

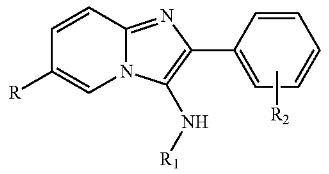

wherein,
R is bromo, methyl, phenyl, nitro, hydrogen or an amide functional group;
$R_1$ is benzyl, 2,6-dimethylphenyl or cyclohexyl; and
$R_2$ is methoxy, benzyloxy or hydroxy.

3 Claims, 6 Drawing Sheets

A

B (a)

(b)

(c)

IMIDAZO[1,2 A] PYRIDINE-6-CARBOXAMIDE DERIVATIVES, THEIR USE FOR THE TREATMENT OF COLON CANCER AND THEIR METHOD OF MANUFACTURE

FIELD OF THE INVENTION

This invention relates to the manufacture of novel chemical compounds which have biological activity, particularly to novel chemical compounds that are cytotoxic against colon cancer cells and colon cancer cell lines.

BACKGROUND OF THE INVENTION

Cancer is considered to be the leading cause of death in developed countries necessitating the development of novel anti-cancer agents. Worldwide colon cancer is one of the most prevalent types of cancer being the fourth most common cancer in men and the third in women. Conventionally, colon cancer can be treated by surgical ablation, however many colon cancers are discovered at an advanced stage when surgery alone is unable to cure the disease. As over 40% of colon cancer patients develop metastases chemotherapy and/or radiotherapy are used as an adjunctive to surgical means in order to treat the disease. However, these techniques are not always effective against highly metastasized stages of the disease and consequently the development of novel therapeutic means effective against advanced stages of colon cancer are essential.

A number of factors influence the risk of developing colon cancer, such as age and diet, although it is predominantly a genetic disease, resulting from DNA mutations. It is caused by the overexpression of oncogenes and the inactivation of tumour suppressor genes.

Currently, a major research initiative is being directed towards the identification and understanding of the biochemical mechanisms by which cell death is initiated. Cells die as a result of necrosis which occurs as a result of injury or by programmed cell death through apoptosis. When DNA is damaged in normal cells, it is either repaired or the cell undergoes apoptosis. In cancerous cells, DNA repair does not often occur and the apoptotic levels are extremely low. Several chemotherapeutic agents have been proven to induce apoptosis through underlying cellular mechanisms. The identification of apoptosis inducers presents a strong basis for the development of potential anti-cancer agents and furthermore, by apoptosis induction the novel compounds may reduce the resistance of colon cancer cells to current therapeutic regimes.

The search for novel drugs to be used in the treatment of colon cancer is essential in combating this life-threatening disease. Large-scale screening of compounds with potential anticancer activity is used to assess a broad range of pharmaceutical compounds, including both naturally occurring and synthesized chemical compounds. The primary aim of in vitro screening programmes is to identify biologically active compounds showing selective activity against certain tumour cell lines. These compounds can then be developed into novel chemotherapeutic drugs for the treatment of different types of cancer.

The use of multi-component chemical reactions in the synthesis of biologically active compounds displaying anti-cancer properties has been an area of prolific research in recent times. One of the classes of compounds that are accessible by multi-component chemical reactions are the imidazo[1,2-a] pyridines.

SUMMARY OF THE INVENTION

In accordance with a first aspect of this invention there is provided at least one novel derivative of the imidazo[1,2-a] pyridine class of compounds of Formula 1, Formula 1

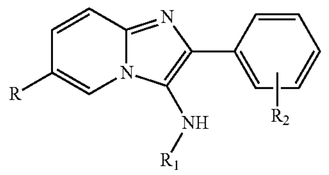

wherein,

R is bromo, methyl, phenyl, nitro, hydrogen or an amide functional group;

$R_1$ is benzyl, 2,6-dimethylphenyl or cyclohexyl; and $R_2$ is methoxy, benzyloxy or hydroxy.

There is further provided for the novel derivative of the imidazo[1,2-a]pyridine class of compounds to have cytotoxic activity against cancer cells or cancer cell lines, particularly colon cancer cells or colon cancer cell lines, more particularly the human colon cancer cell lines HT-29 and Caco-2.

There is further provided for each novel derivative of the imidazo[1,2-a]pyridine class of compounds to have cytotoxic activity against cancer cells or cancer cell lines, particularly colon cancer cells or colon cancer cell lines, more particularly the human colon cancer cell lines HT-29 and Caco-2, whilst concomitantly having a minimalistic effect against white blood cells.

There is further provided for the use of at least one novel derivative of the imidazo[1,2-a]pyridine having the Formula 1 in the manufacture of a medicament to treat cancer, preferably colon cancer, comprising administering said medicament to a patient in need thereof.

There is further provided for a pharmaceutical compound comprising at least one novel derivative of the imidazo[1,2-a]pyridine having the Formula 1.

In accordance with a second aspect of the invention there is provided for a method of treating cancer, preferably colon cancer, in a human or animal which comprises administering to the human or animal an effective amount of the compound of Formula 1.

There is further provided for a method of treating cancer, preferably colon cancer, in a human or animal which comprises administering to the human or animal an effective amount of the pharmaceutical compound.

In accordance with a third aspect of this invention there is provided a method for manufacturing a novel derivative of the imidazo[1,2-a]pyridine class of compounds comprising using a multi-component coupling reaction.

There is further provided for the method to comprise a three component coupling reaction employing the use of a catalyst.

There is further provided for the three component coupling reaction to utilize at least aminopyridines, aromatic aldehydes and at least one type of isocyanide and a catalyst where the catalyst is preferably Montmorilionite clay K10 or scandium(III)triflate.

Preferably the three component coupling reaction comprises the use one compound of the group of 5-substituted 2-aminopyridines: 5-nitroaminopyridine, 5-bromoaminopyridine and nicotinamide; one compound of the group of isocyanides: cyclohexylisocyanide, 2,6-dimethylphenylisocyanide and benzylisocyanide; and one compound of the group of aromatic aldehydes: 3,5-dimethoxybenzaldehyde or 3,5-dibenzyloxybenzaldehyde.

EXAMPLES OF THE INVENTION

Figure 1:
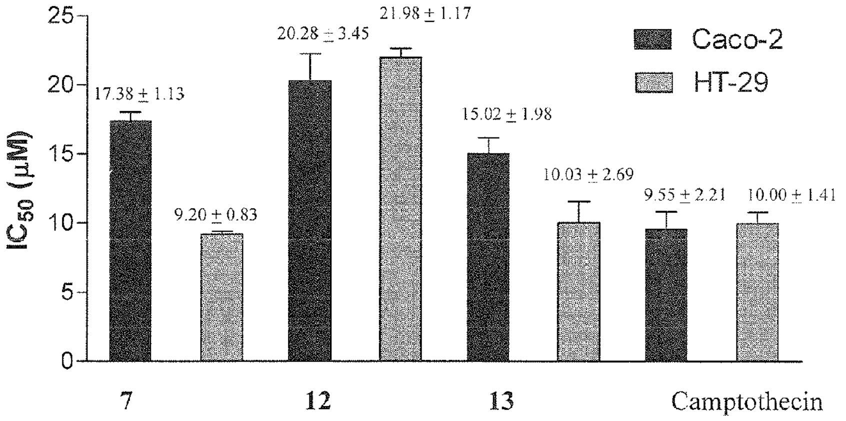
FIG. 1 shows $IC_{50}$ values for (A) compounds 7, 12, 13 and (B) compounds 14, 4, 3, 6, and the positive control camptothecin on the Caco-2 and HT-29 cell line.
Figure 1:
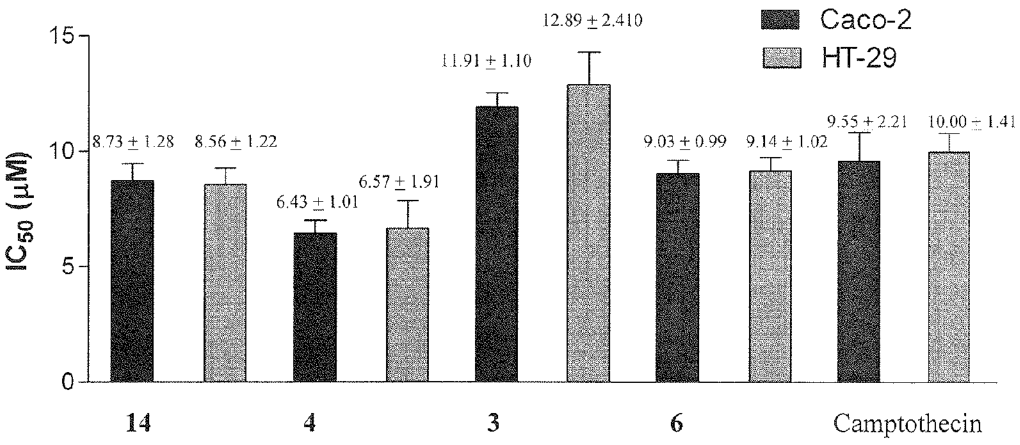

The above and additional features of the invention will be described below with reference to non-limiting examples:

Preparation Examples

Preparation examples to manufacture and to identify novel imidazo[1,2-a]pyridine analogues with anticancer activity, specifically targeted against colon cancer are discussed below:

Attempts were made to assemble a number of imidazo[1,2-a]pyridines that could show biological activity against cancer cell lines, specifically colon cancer cell lines. Derivatives of imidazo[1,2-a]pyridine have been produced using modern synthetic methods using three component reaction entailing the use of aminopyridines, aromatic aldehydes isocyanides and a catalyst such as scandium (III) triflate or Montmorillonite clay K10 (Scheme 1):

Scheme 1.

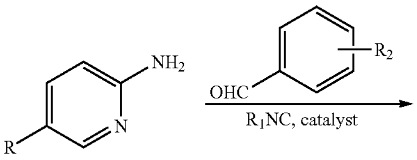

-continued

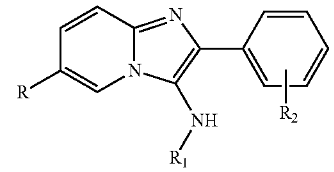

More specifically, mixing a variety of commercially available 5-substituted 2-aminopyridines or aminopyridine with either cyclohexylisocyanide or 2,6-dimethylphenylisocyanide, and in one case benzylisocyanide, and a variety of substituted aromatic aldehydes in the presence of Montmorillonite clay K10 afforded imidazo[1,2-a]pyridines labeled compounds 1-13 in the unoptimized yields shown in Scheme 2. All of these reactions were readily carried out and could be achieved by stirring all the reagents and catalyst in a round bottom flask exposed to the atmosphere. All products were characterized by $^1H$, $^{13}C$ NMR spectroscopy as well as by HRMS, although a number of the products were not that soluble in deuterated organic solvents traditionally used for NMR spectroscopy.

Scheme 2.

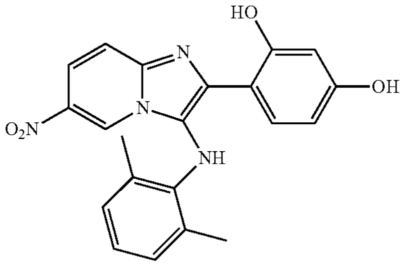

1.11%

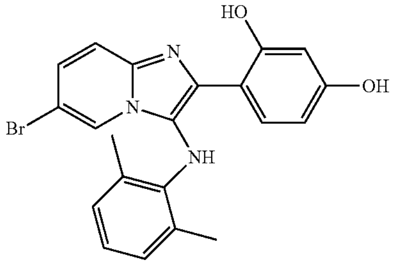

2.74%

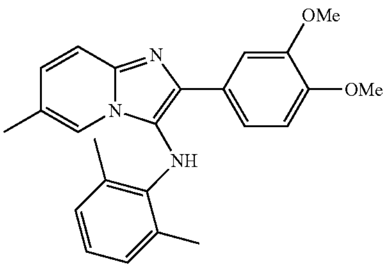

3.42%

-continued

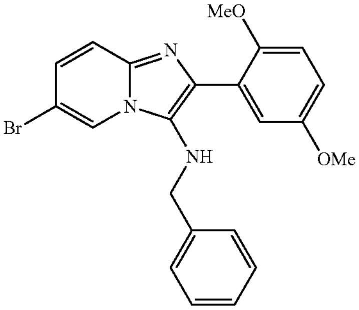 [SMILES: COc1ccc(OC)c(-c2nc3ccc(Br)cn3c2NCc2ccccc2)c1]

4.67%

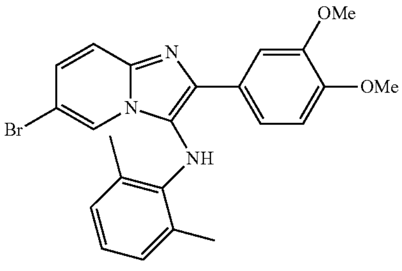

6.67%

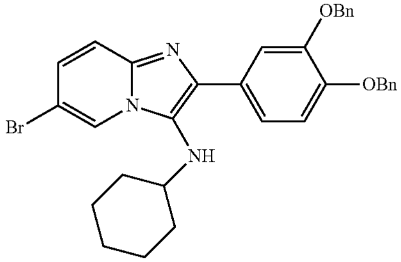

5.39%

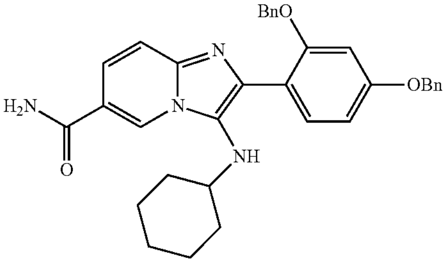

7

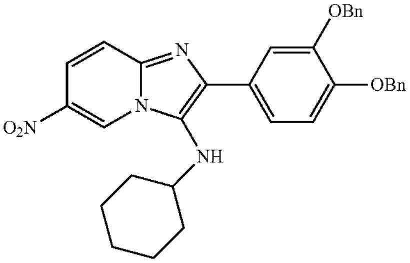

8.43%

-continued

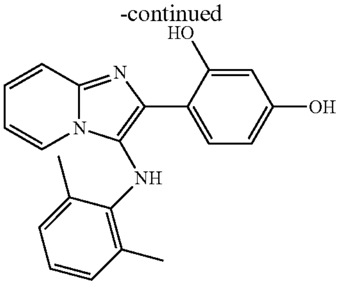

9

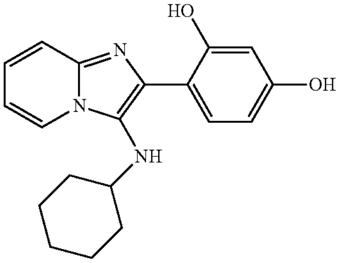

10

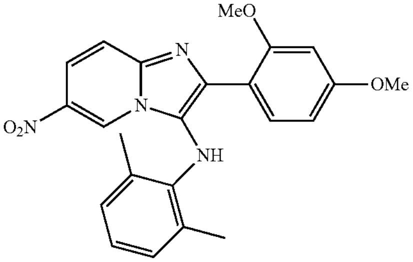

11.56%

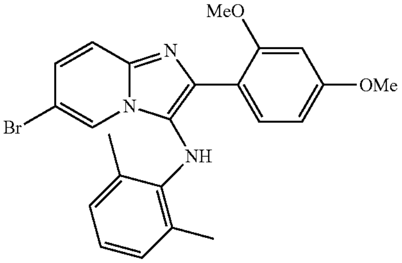

12

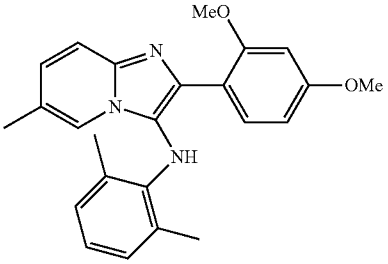

13.77%

As a number of the imidazo[1,2-a]pyridines contained a bromine atom, it is believed that this could be used as a handle for carbon-carbon coupling reactions such as the Suzuki reaction. Using this methodology, further variety could be made on the imidazo[1,2-a]pyridine nucleus. For example, exposure of 6 to phenylboronic acid in the presence of catalytic $Pd(PPh_3)_4$ afforded 14 in a yield of 46% (Scheme 3). Both 6 and 14 were crystalline and their structures suitable to be solved by single crystal X-ray diffraction.

Scheme 3 Reagents and conditions

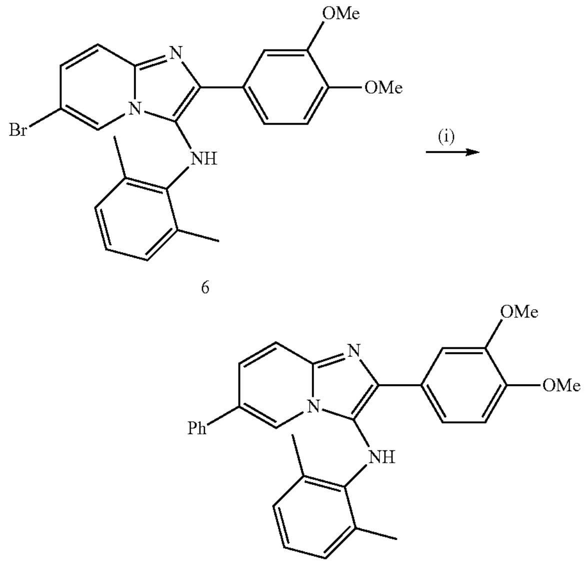

6

14

(i) 10% $Pd(PPh_3)_4$, $PhB(OH)_2$, 2M aq. $Na_2CO_3$, DME/EtOH, 46%.

Use Examples

Biology:

The effects on cell viability to determine whether the imidazo[1,2-a]pyridine derivatives induced cell death in colon cancer cell lines were evaluated by metabolic and flow cytometry assays. Measuring the effects of the derivatives on in vitro cell viabilities is accomplished by the exposure of a cell population to the derivative and then monitoring the enzymatic reduction of MTT to formazan in the mitochondria of living cells. The apoptosis assay monitors cell membrane translocation events and the accessibility of nuclear material in response to extracellular disruptions, and the various stages of apoptosis are then quantified by flow cytometry. A colorimetric assay was used to determine the expression levels of caspase 3 and 8 and a JC-1 flow cytometry Mitochondrial Membrane Potential Detection kit was used to indicate whether apoptotic induction was associated with a depolarisation of the membrane potential. Cytochrome c fractions in the mitochondrial and cytoplasmic fractions were determined by an Enzyme Immunometric Assay (EIA) kit.

a) Effects on Cell Viability of HT-29 and Caco-2 Cells

The colon cancer cells were initially exposed to the different imidazo[1,2-a]pyridines compounds at 100 μM (final concentration in the well) at 37° C. for 24 hours using an MTT assay for cell viability quantification. A compound was considered active when it reduced the growth of the cell lines to 50% or less. FIGS. 1A and 1B report the $IC_{50}$ values (molar concentration that inhibited growth by 50%) obtained from the active compounds. $IC_{50}$ values showed no significant difference ($p>0.05$, $p=0.665$) between 7 (9.20±0.83 μM), 13 (10.03±2.69 μM) and camptothecin (9.99±1.41 μM) on the HT-29 cell line, while 12 showed a significantly ($p<0.05$, $p=0.005$) higher $IC_{50}$ value of 21.98±1.17 μM. $IC_{50}$ values determined for all derivatives on the Caco-2 cell line were significantly higher ($p<0.05$, $p=0.001$) than for camptothecin (9.55±2.21 μM). Compound 4 was more effective than camptothecin in inhibiting both Caco-2 and HT-29 activity, yet the difference in cell viability was not significant ($p>0.05$, $p=0.057$). $IC_{50}$ values obtained for 14, 4 and 6 were lower than the $IC_{50}$ values obtained for camptothecin. There was no significant difference ($p>0.05$, $p=0.107$) between the $IC_{50}$ values of 14, 6 and camptothecin.

The bars represent the mean±SEM of the $IC_{50}$ values from three MTT assays carried out for each derivative. The HT-29 and Caco-2 cells were exposed to the novel imidazo[1,2-a]pyridine class of compounds according to the invention in concentrations ranging from 5 μM to 100 μM for 24 hours.

b) Effects on Cell Viability of White Blood Cells

Cell viability was determined by the MTT assay after the white blood cells were exposed to the novel compounds for 24 hours at an initial concentration of 100 μM. Camptothecin was used as a positive control for cytotoxicity. The results obtained are summarized in Table 1. Camptothecin was significantly ($p<0.05$) more effective than all the novel compounds in inhibiting white blood cell activity when tested at 100 μM. None of the selected novel compounds resulted in a 50% or more reduction of white blood cells.

TABLE 1

Percentage cell viability of the white blood cells treated with 100 μM of the cytotoxic novel compounds and the control camptothecin, for 24 hours.

| Compound | White Blood Cell Viability % |
|---|---|
| 7 | 93.834 ± 0.271% |
| 12 | 96.311 ± 5.023% |
| 13 | 97.479 ± 1.178% |
| 14 | 77.345 ± 1.005% |
| 4 | 88.943 ± 1.996% |
| 3 | 76.176 ± 0.567% |
| 6 | 83.762 ± 1.389% |
| Camptothecin | 33.782 ± 2.031% |

c) Effects on Cell Death of HT-29 and Caco-2 Cells

Figure 2:
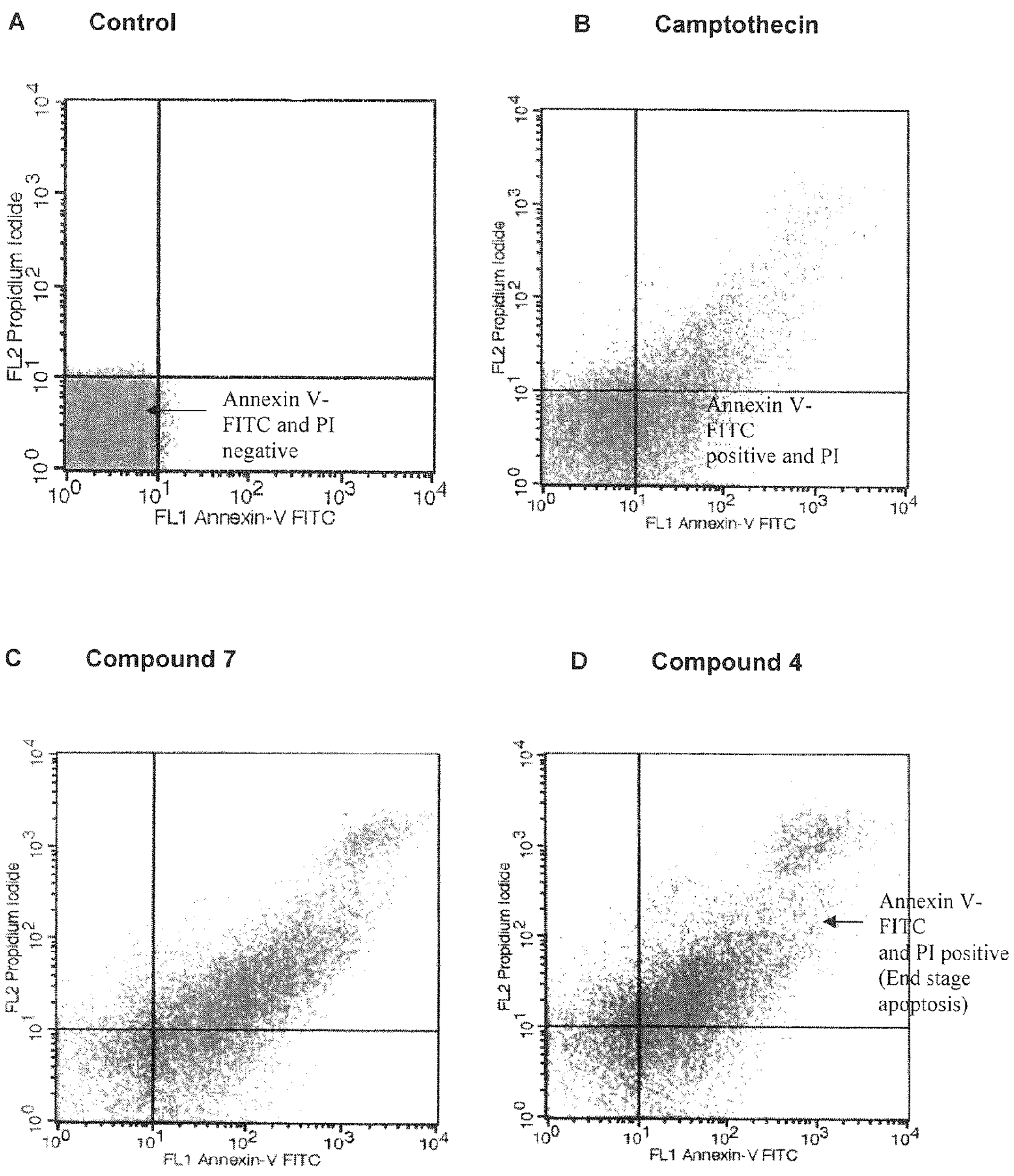
FIG. 2: shows annexin V-FITC staining in control and apoptotic HT-29 cells induced by compound 7, compound 4 and camptothecin.

FIG. 2 shows that apoptosis was induced after addition of the synthetic compounds. The assay was performed by evaluating cells that were stained using fluorescein isothiocyanate (FITC)-labelled Annexin V (green fluorescence) as well as dye exclusion of Propidium iodide (PI)I (negative for red fluorescence). The untreated cells were mainly Annexin V-FITC and PI negative, indicating that they were viable and not undergoing apoptosis. After a 24 hour exposure to the compounds as well as camptothecin, there were primarily two populations of cells: viable, non-apoptosing cells (Annexin V-FITC and PI negative) and cells undergoing apoptosis (Annexin V-FITC positive and PI negative). A small population of cells (18.17%) was observed to be Annexin V-FITC and PI positive, indicating that they were in end-stage apoptosis (FIG. 2).

d) Enzyme Activity Assays

Figure 3:
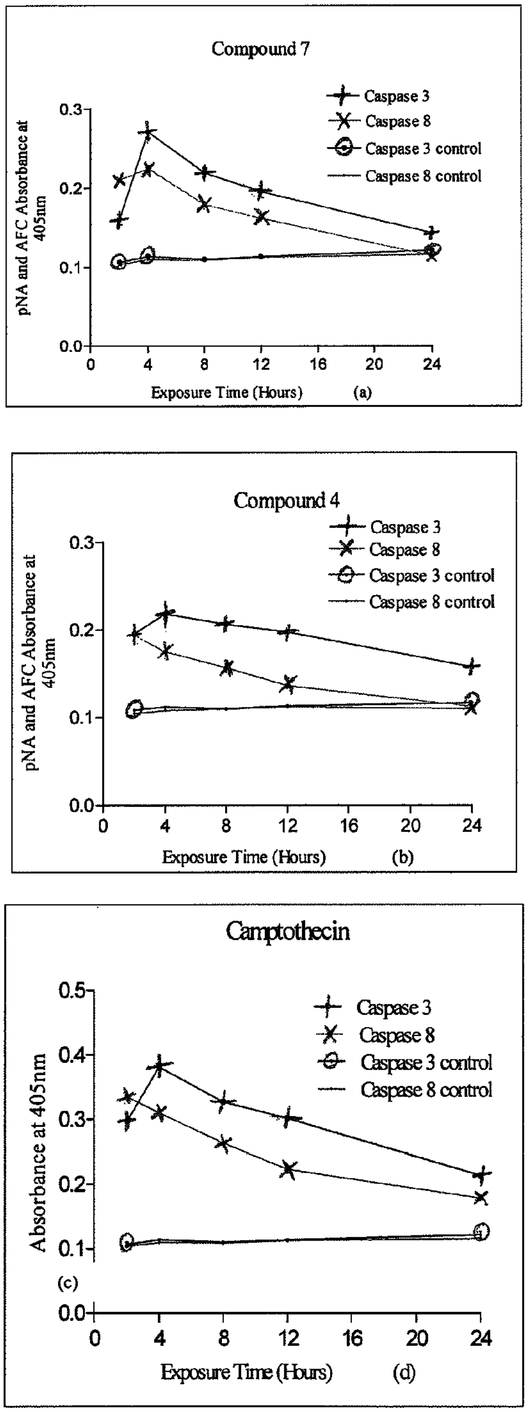
FIG. 3: shows time-dependent induction of caspase 3 and caspase 8 activity by (a) compound 7, (b) compound 4, and (c) camptothecin in (A) HT-29 cells and (B) Caco-2 cells. Each point represents the mean and standard deviation of the triplicate values of Caspase 3 and Caspase 8 expression levels after cell exposure to the selected compounds over 2 hours, 4 hours, 8 hours, 12 hours and 24 hours.
Figure 3:
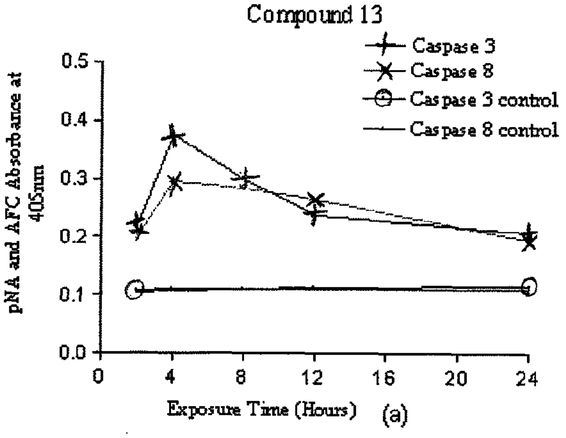
Figure 3:
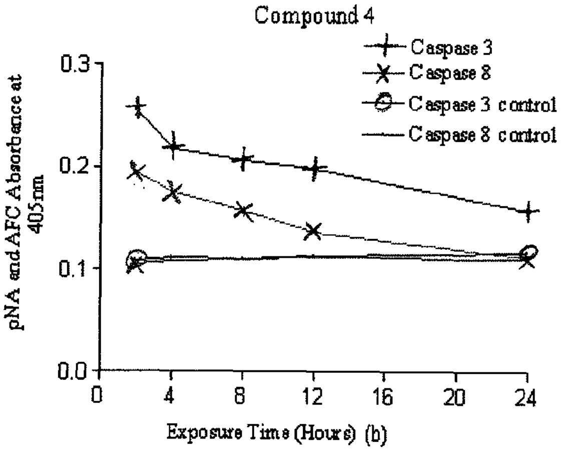
Figure 3:
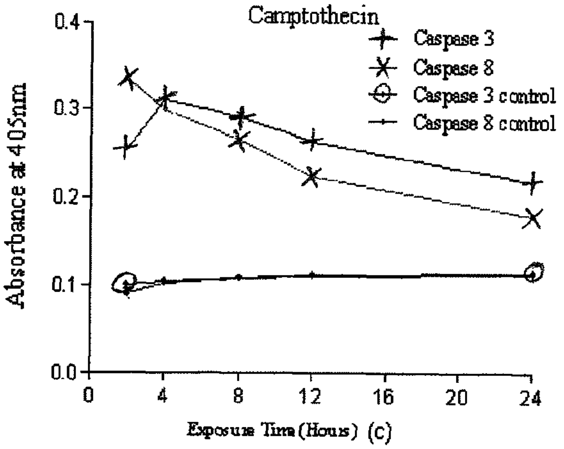

As it is well known that caspases play a vital role in the execution of apoptosis, the level of caspase 3 and caspase 8 enzymatic activity in the cell lysates were determined using a caspase 3 and caspase 8 colorimetric assay kit (FIGS. 3A and B). Maximal caspase 8 expression in HT-29 cells was observed within 2 hours of exposure to all the CDK compounds. After 2 hours, the activity of caspase 8 declined, whereas that of caspase 3 increased, indicating that the proteolytic phase of apoptosis was initiated. Maximal caspase 3 expression in the HT-29 cells was observed after 8 hours of exposure to 7 and 13, and 4 hours of exposure to 12. Maximal caspase 8 expression in the HT-29 cells was observed within 2 hours of exposure to 14, 4 and 6, and within 4 hours after exposure to 3. Maximal caspase 3 expression in the HT-29 cells was observed after 2 hours of exposure to 4 and 6, and after 4 hours of exposure to 14 and 3. These results highlight the key role of caspase activation in the novel compounds' induced cell death.

Caspase 3 levels increased between 2 hours and 4 hours after exposure to 7, 13 and camptothecin and between 2 hours and 8 hours after exposure to 12. Caspase 8 levels were at their peak within 4 hours of exposure to 7, 12 and 13. Since caspase 3 is the main effector caspase in the apoptotic cycle, high levels of this enzyme indicates early apoptosis after exposure to camptothecin, 7 and 13. There was no significant increase ($p>0.05$, $p=0.107$) in the levels of caspase 3 and caspase 8 in the untreated cells after 24 hours. High levels of caspase 8 were observed in the HT-29 cells within 2 hours of exposure to 14, 4 and 6, and within 4 hours of exposure to 3. High caspase 3 levels were observed in the HT-29 cells after 2 hours of exposure to 14, 4 and 6, and after 4 hours of exposure to 3. The high levels of caspase 3 at 2 and 4 hours indicate that apoptosis was initiated fairly early after exposure to these compounds. 14, 4 and 6 initiated apoptosis at an earlier stage than camptothecin. There was no significant increase ($p>0.05$, $p=0.107$) 4 in the levels of caspase 3 and caspase 8 in the untreated cells after 24 hours.

Caspase 3 levels increased between 2 hours and 4 hours after exposure to 7, 13 and camptothecin and between 2 hours and 8 hours after exposure to 12. High levels of Caspase 8 in the Caco-2 cells were observed within 4 hours of exposure to 7, 12 and 13. There was no significant increase ($p>0.05$, $p=0.113$) in the expression levels of caspase 3 and caspase 8 in the untreated cells after 24 hours. High levels of caspase 8 were observed in the caco-2 cells within 2 hours of exposure to 14, 4 and 6, and within 4 hours of exposure to 3. High caspase 3 levels were observed in the caco-2 cells after 2 hours of exposure to 14, 4 and 6 and after 4 hours of exposure to 3. The effects of these agents on the caspase 3 and caspase 8 levels in caco-2 cells were very similar to the effects on the HT-29 cells. The high levels of caspase 3 at 2 and 4 hours indicate that apoptosis was initiated fairly early after exposure to these compounds. There was no significant increase ($p>0.05$, $p=0.113$) in the expression levels of caspase 3 and caspase 8 in the untreated cells after 24 hours.

e) Effects on the Mitochondrial Membrane Potential

Figure 4:
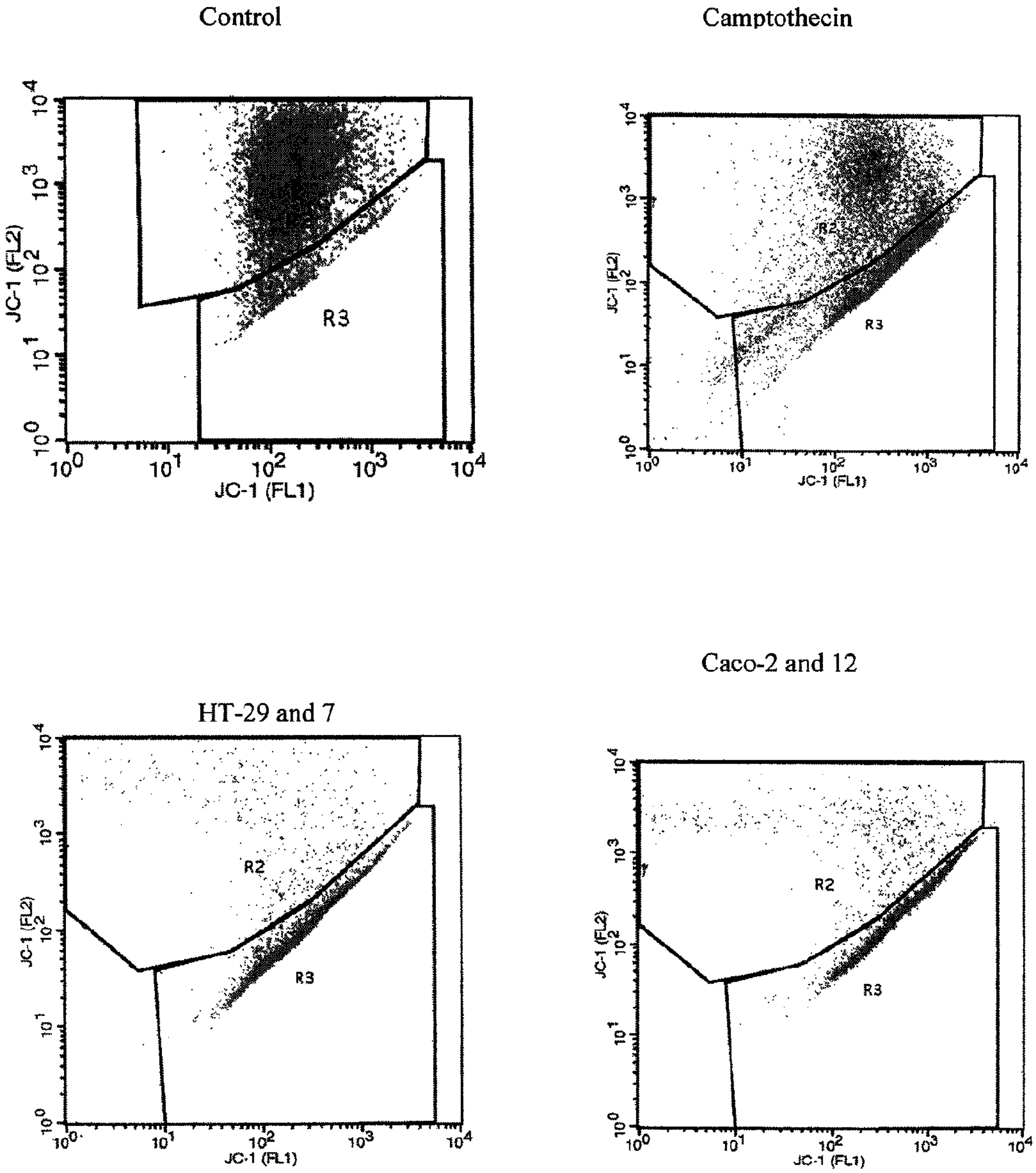
FIG. 4: shows JC-1 staining in control and apoptotic cells induced by camptothecan, compound 7 and compound 12.

The dysfunction of the mitochondria is believed to be an important step in the commitment of the cell to apoptosis. To assess whether disruption of the mitochondrial transmembrane potential ($\Delta\psi$) was involved in the apoptotic action of the novel imidazo[1,2-a]pyridines, the HT-29 and Caco-2 cells were treated for 24 hours with 100 μM of the novel compounds and then analysed by flow cytometry by using the cationic fluorescent dye 5,5',6,6'-tetrachloro-1,1',3,3'-tetraethylbenzimidazolcarbocyanine iodide (JC-1) to measure mitochondrial membrane depolarization in intact viable cells. Compound 7 was shown to be the most potent inducer of apoptosis in the HT-29 cells (FIG. 4), with 79.62% of cells undergoing apoptosis in comparison to 20.33% of healthy cells remaining after treatment. Compound 12 was the most effective apoptotic inducer in the Caco-2 cells with an average of 81.91% of cells undergoing apoptosis. The results show that apoptosis induced by the imidazo[1,2-a]pyridine derivatives is associated with depolarisation of the mitochondrial membrane.

f) Effects on the Release of Cytochrome C

Figure 5:
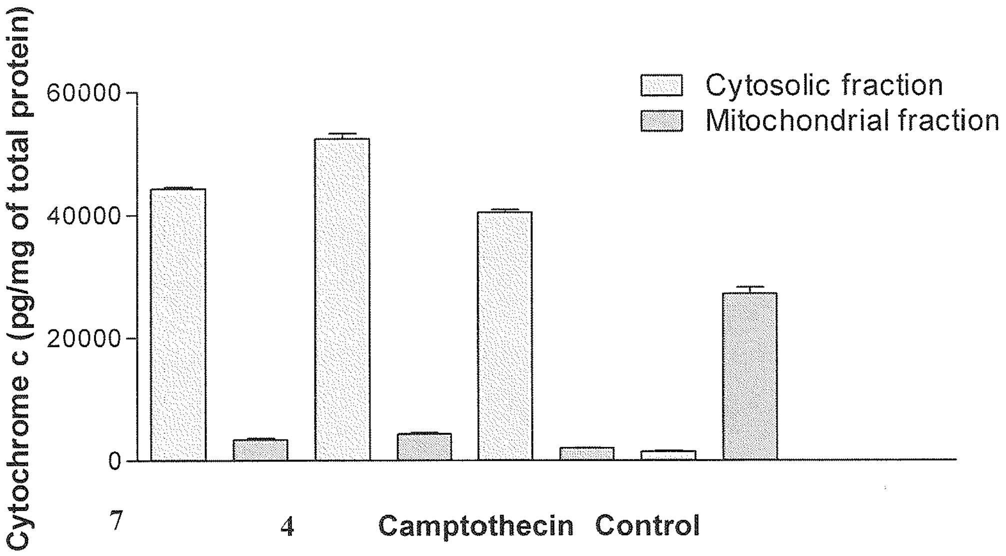
FIG. 5: shows concentrations of cytochrome c (pg/mg) in the cytosolic and mitochondrial fractions of HT-29 cells after treatment with compound 7, compound 4 and camptothecin for 24 hours.

Cytochrome c is an electron transport protein which is normally located between the inner and outer mitochondrial membrane. It has been shown to shift from the mitochondria to the cytoplasm during apoptosis. A quantitative concentration of cytochrome c in the cell lysates was determined by a human cytochrome c Titerzyme Enzyme Immunometric Assay kit (FIG. 5). Cytochrome c concentrations were higher in the cytosolic protein fractions than in the mitochondrial protein fractions of the HT-29 and Caco-2 cells that were treated with the active compounds. The untreated cells had a larger concentration of cytochrome c in the mitochondrial fraction than in the cytosolic fraction.

Among the selected compounds that we tested against the HT-29 and Caco-2 cell lines, 7 and 4 are cytotoxic and elicit apoptosis in the colon cancer cells at low micromolar concentrations. The compounds showed a degree of selective cytotoxicity against the cancer cell lines, with minimal cytotoxicity against the white blood cells. The proteolytic phase of apoptosis was initiated after 2 hours after treatment with the selected compounds. The selected compounds are also associated with a marked reduction in the mitochondrial membrane potential $\Delta\psi$ as well as causing an increase in cytochrome c levels within the cytosolic fraction of the cells. The induction of apoptosis is considered to be the main mechanism underlying the therapeutic efficacy of anticancer drugs, hence the present results suggest that the imidazo[1,2-a]pyridine derivatives may successfully be developed into novel chemotherapeutic drugs for the treatment of colon cancer cells.

Experimental Procedures

Biological Cell Lines

The study made use of two colonic carcinoma cell lines, namely the HT-29 and Caco-2 cell lines. The HT-29 and Caco-2 cell lines were obtained from Highveld Biological, South Africa. Both cell lines were cultured in Dulbecco's Modified Eagles Medium (DMEM) (Highveld Biological, South Africa) and supplemented with 5% heat-inactivated heat-inactivated foetal bovine serum (FBS). 1 ml 10 kU penicillin G/10 mg streptomycin sulphate (pen/strep) (Highveld Biological, South Africa) and 0.4% 100 mM sodium pyruvate per 500 ml DMEM were added after filter sterilisation.

Determining Cell Viability Via the MTT Assay

The two colon cancer cells were counted and diluted into fresh media at concentrations of 30 000 cells/well and an aliquot of 180 μl was seeded to each well in a 96-well plate. The plates were then placed in an incubator (37° C., 5% $CO_2$, volume fraction) and the cells were allowed to divide for a period of 24 hours.

The cells were exposed to the different classes of synthetic compounds at 100 μM (final concentration in the well) at 37° C. for 24 hours using an MTT assay for cell viability quantification. After the 24 hour incubation, the plates were removed from the incubator, and an aliquot of 50 μl 0.5% MTT (USB, USA) in 1 mM PBS (pH 7.4) was layered on the media. The plates were incubated for 2 hours at 37° C. The plates were than centrifuged at 3000 rpm (Afrox Sorvall T 6000D) for 5 minutes. Following centrifugation, the medium was very carefully aspirated. Formazan crystals were dissolved in 200 μl DMSO. The absorbance was then read at 540 nm using the Absorbance Labsystems Multiskan MS, version 2.4. The controls used in the assay consisted of i) medium alone without cells, ii) medium with or without the tested compounds and iii) medium with Camptothecin.

Compounds showing cytotoxicity at a concentration of 100 μM were further diluted to obtain an $IC_{50}$ concentration. All tests were performed in triplicate.

The $IC_{50}$ values for the two cell lines are shown in FIG. 1 with all of the compounds showing low micromolar activity in the two cell lines examined.

Statistics

Statistically significant differences between the control and experimental samples were determined with the Prism3 Instat package, using ANOVA. Student-Newman-Keuls test. The values are expressed as mean+/− standard deviation of the mean. Significance was set at $p<0.05$.

Assessment of Apoptosis:

Annexin V

One of the most important stages of apoptosis involves the attainment of surface changes by dying cells that would eventually result in the uptake of these cells by phagocytes. Many studies have shown that cells undergoing apoptosis break up the phospholipid asymmetry of their plasma membrane and expose phosphatidylserine (PS), which is translocated to the outer layer of the membrane. Annexin V is a useful tool in detecting apoptotic cells since it binds preferentially to negatively charged phospholipids such as PS. The translocation of PS occurs in both necrosis and apoptosis, hence Annexin V was combined with PI. The cell staining was assessed using fluorescein isothiocyanate (FITC)-labelled Annexin V (green fluorescence) as well as dye exclusion of propidium iodide (PI) (negative for red fluorescence). It is possible to detect and quantitate the apoptotic cells on a single-cell basis by flow cytometry and to identify the intact cells (FITC−PI−), early apoptotic (FITC+PI−), late apoptotic or necrotic cells (FITC+ PI+) (Vermes et al., 1995).

The treated cells were washed with 0.1 M phosphate buffered saline (PBS) (pH 7.4). FITC-Annexin V was diluted to a concentration of 1 mg/ml in binding buffer and the cells were resuspended in 1 ml of this solution. Thereafter, the cells were incubated for 10 minutes in the dark at room temperature. 0.1 ml of Propidium Iodide solution was added to the cell suspension to yield a final concentration of 1 mg/ml. The cells were analysed by flow cytometry and the data was displayed as a two-color dot plot with FITC-Annexin V (green fluorescence, X axis) vs. PI (red fluorescence, Y axis).

Colorimetric Assay for Caspase Detection

The activation of caspases initiates apoptosis in mammalian cells. Caspase 3 and Caspase 8 were detected using the CPP32 and FLICE colorimetric Assay kits, respectively. The following method (obtained from Biovision research products) was performed.

The treated HT-29 and Caco-2 cells were harvested and resuspended in 50 μl of chilled cell lysis buffer and incubated on ice for 10 minutes. The cells were centrifuged for 1 minute (10000 g) and the supernatant (cytosolic extract) was transferred to a fresh tube and placed on ice. The protein concentration was assayed using the Biorad assay method. 100-200 μg protein to 50 μl cell lysis buffer was diluted for each assay. 50 μl of 2× Reaction buffer (containing 10 mM DTT) was added to each sample. 5 μl of 4 mM IETD-pNA substrate for Caspase 8 and 5 μl of 4 mM DEVD-pNA substrate for Caspase 3 was added to each sample and incubated at 37° C. for 1-2 hours. The samples were read at 405 nm in the microtiter plate reader. Time dependent studies were performed for protease activity by attaining results 2, 4, 6, 12, and 24 hours after treatment with the compounds.

Mitochondrial Membrane Potential

When energy is released during the oxidation reactions in the mitochondrial respiratory chain, it is stored as a negative electrochemical gradient across the mitochondrial membrane. Under these situations, the mitochondrial membrane potential ($\Delta\psi$) is polarized. During the early stages of apoptosis, a collapse of the $\Delta\psi$ which results in a depolarized $\Delta\psi$, is sometimes noticed. The collapse of the $\Delta\psi$ during apoptosis was noticed in several studies and it has thus been suggested that the depolarisation of the mitochondria is one of the first events which occurs in apoptosis and could be a prerequisite for the release of cytochrome c. Since the collapse of the $\Delta\psi$ does not always occur in apoptosis, the depolarisation of the $\Delta\psi$ may only be a cause of or associated with apoptosis in some systems. The changes in $\Delta\psi$ have also been noticed during necrosis (depolarisation) and cell cycle arrest (hyperpolarisation). Understanding the $\Delta\psi$ and how it alters during apoptosis and necrosis, may assist in determining the function of the mitochondria in these and other cellular processes. The fluorescent mitochondrial-specific cationic dye 5,5',6,6'-tetrachloro-1,1',3,3'-tetraethylbenzimidazolcarbocyanine iodide (JC-1) was used to measure the collapse of the electrochemical gradient across the mitochondrial membrane.

The HT-29 and Caco-2 cells were plated in 24-well microtitre plates (Nunc. Denmark) at a density of approximately $1.2\times10^6$ cells per ml. A background control of complete culture medium was included in each experiment and Camptothecin was used as a positive control at a concentration of 100 μg/ml. The plated cells were incubated at 37° C. for 24 hours and then treated with the corresponding compounds for another 24 hours. The treated cells were then lifted, washed with PBS and transferred into sterile eppendorfs. The cells were centrifuged at 400 g for 5 minutes and the supernatant was discarded. 0.5 ml of freshly prepared JC-1 working solution (125 μl JC-1, 12.375 ml prewarmed 1× assay buffer) was added to each pellet. The cells were resuspended in the JC-1 working solution and then incubated for 15 min at 37° C. in a $CO_2$ incubator. The cells were washed twice in 1× assay buffer and centrifuged at 400 g for 5 minutes after each washing step. Each cell pellet was resuspended in 0.5 ml of assay buffer and the cells were analysed by flow cytometry using excitation/emission filters of 485/540 nm (green/FL-1); 540/590 nm (red/FL-2). The ratio of red/green fluorescence was calculated.

Detection of the Release of Cytochrome c Determination

A quantitative concentration of cytochrome c in the cell lysates was determined by a human cytochrome c Titerzyme Enzyme Immunometric Assay kit. The kit uses a monoclonal antibody specific for cytochrome c, a biotinylated detecting antibody and Alkaline phosphatase-conjugated Streptavidin to provide a colorimetric detection that enables a quantitative determination of the cytochrome c in the cell lysates. The treated HT-29 and Caco-2 cells were harvested and rinsed with ice-cold phosphate buffered saline. The cytosolic and mitochondria protein were isolated respectively according to the protocol provided by the Mitochondria isolation kit (Assay designs, Inc).

The cell pellet was resuspended with Digitonin Cell Permeabilization Buffer, vortexed and incubated on ice for 5 minutes at 4° C. The supernatants were saved since they contained the cytosolic fraction of cytochrome c and the remaining pellet was resuspended with RIPA Cell Lysis Buffer 2, vortexed and incubated on ice for 5 minutes. The lysate was vortexed and centrifuged at 10,000 g for 10 minutes at 4° C.

The protein concentration from each fraction was determined by a Bio-Rad protein assay kit. The fractions were run in the assay and the resulting pictogram determinations were divided by the protein concentration.

A native human cytochrome c Standard was provided in the kit in order to create a standard curve. The standard was solubilised in the provided Assay Buffer to create a range of cytochrome c standard dilutions with final concentrations of 900, 450, 225, 112.5, 56.25 and 28.13 pg/ml. 100 μl of the assay buffer, standards and samples were pipetted into the appropriate wells on the provided 96 well microtitre plate. The plate was sealed and incubated at room temperature on a plate shaker for 1 hour at 500 rpm. The contents of the well were emptied and 400 μl of wash solution was added to every well. The wash was repeated 3 times for a total of 4 washes. After the final wash, 100 μl of yellow antibody was pipetted into each well except the blank. The plate was sealed and incubated at room temperature on a plate shaker for 1 hour at 500 rpm. The contents of the well were removed and the wash step was repeated. 100 μl of blue antibody was added to each well except the blank and the plate was sealed and incubated at room temperature on a plate shaker for 30 minutes at 500 rpm. The contents of the well were removed and the wash step was repeated. 100 μl of Substrate Solution was added to each well and incubated at room temperature on a plate shaker for 45 minutes at 500 rpm. 25 μl Stop Solution was added to each well and the optical density was measured at 405 nm. The optical density of the Blank was subtracted from all the readings.

The absorbances of the standard dilutions at a wavelength of 405 nm minus the blank were used to create a standard curve of Optical Density (405 nm) versus Cytochrome c concentration (pg/ml). The unknown cytochrome c concentrations of the cytoplasmic and mitochondrial fraction samples were determined from the standard curve.

The invention claimed is:

1. A chemical compound of Formula 1,

Formula 1

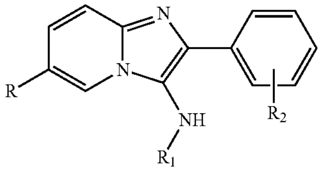

wherein,

R is bromo, methyl, phenyl, nitro or $CONH_2$;

$R_1$ is 2,6-dimethylphenyl or cyclohexyl; and $R_2$ is two methoxy groups, two benzyloxy groups or two hydroxy groups.

2. The compound of claim 1, which is selected from the group consisting of:

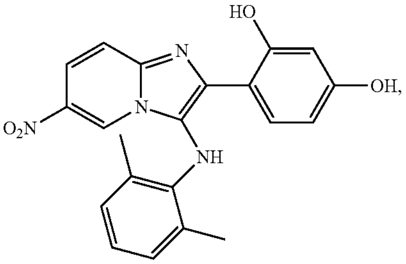

-continued

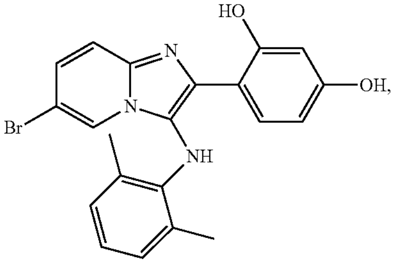

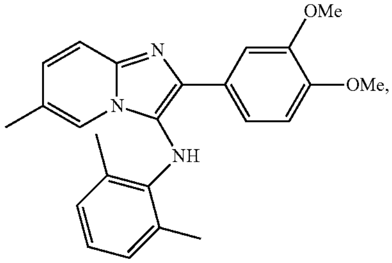

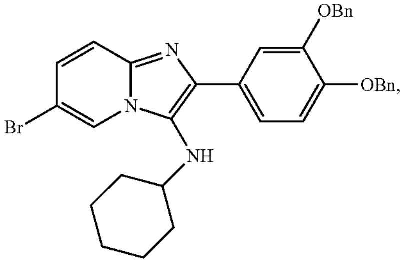

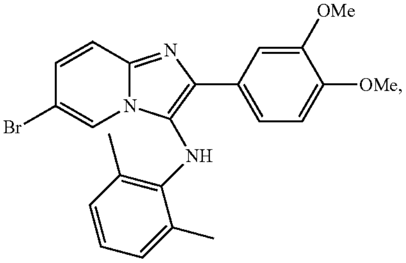

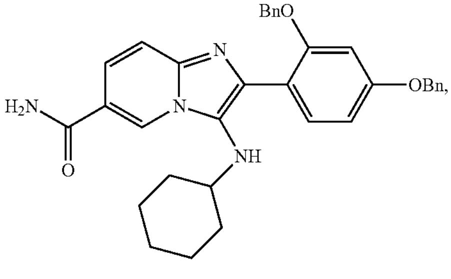

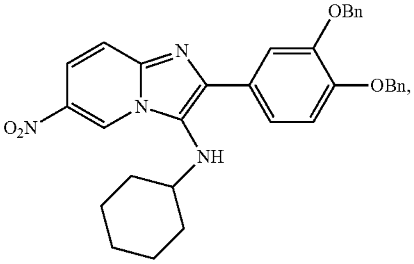

-continued
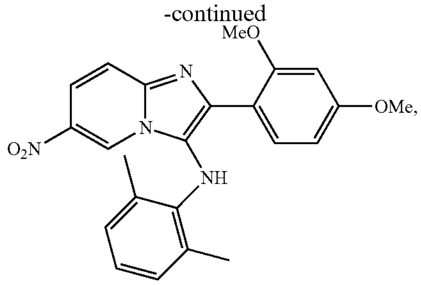
,
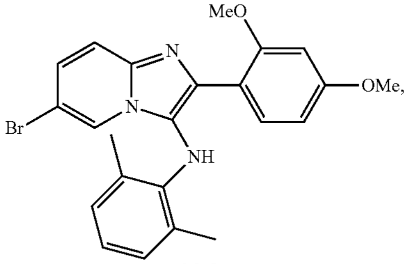
,
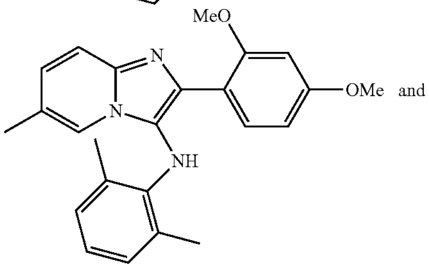
and
-continued
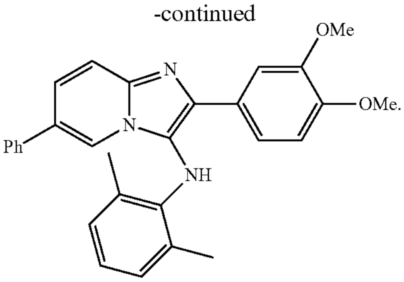
.
3. A compound of the formula:
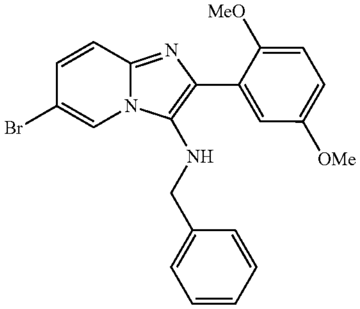
* * * * *